United States Patent
Enright et al.

(12)

(10) Patent No.: US 10,007,652 B1
(45) Date of Patent: Jun. 26, 2018

(54) METHOD FOR REUSING AND DYNAMICALLY FILTERING CONTENT FOR STRUCTURED DOCUMENT CONSTRUCTION

(71) Applicant: ALLSCRIPTS SOFTWARE, LLC, Chicago, IL (US)

(72) Inventors: Nathan Enright, Debary, FL (US); Robert Taylor, Media, PA (US)

(73) Assignee: Allscripts Software, LLC, Chicago, IL (US)

( * ) Notice: Subject to any disclaimer, the term of this patent is extended or adjusted under 35 U.S.C. 154(b) by 532 days.

(21) Appl. No.: 14/460,608

(22) Filed: Aug. 15, 2014

Related U.S. Application Data (60) Provisional application No. 61/866,329, filed on Aug. 15, 2013.

(51) Int. Cl.
    *G06F 17/00*      (2006.01)
    *G06F 17/24*      (2006.01)

(52) U.S. Cl.
    CPC ................... *G06F 17/243* (2013.01)

(58) Field of Classification Search
    CPC .... G06F 19/363; G06F 19/321; G06F 17/243; G06Q 50/22; G06Q 50/24
    USPC ........................................ 715/221, 224, 225
    See application file for complete search history.

(56) References Cited

U.S. PATENT DOCUMENTS

| | | | |
|---|---|---|---|
| 7,885,440 B2 * | 2/2011 | Fram ..................... | A61B 6/463 382/128 |
| 8,019,138 B2 * | 9/2011 | Reicher ................ | G06F 19/321 345/556 |
| 8,645,861 B2 * | 2/2014 | Rumak ................. | G06F 19/366 715/810 |
| 9,075,899 B1 * | 7/2015 | Reicher ................ | G06F 19/321 |
| 9,177,110 B1 * | 11/2015 | Fram ................... | G06F 19/3487 |
| 2010/0138239 A1 * | 6/2010 | Reicher ................ | G06F 17/243 705/3 |

* cited by examiner

*Primary Examiner* — Stephen Hong
*Assistant Examiner* — Matthew Lugwig
(74) *Attorney, Agent, or Firm* — Loza & Loza, LLP; Peter Zura (57) ABSTRACT

An aspect of the present invention relates to a method for dynamically constructing a pre-populated note template comprising receiving a context from a user and determining whether there are any note templates that match an initial criteria including the received context. A note template is then loaded based on the determination of matching note templates. If there are one or more sections in the loaded template, for each section in the loaded template, determine if there are any forms for the section that match the context. A pre-populated Note template is then loaded including any matching forms.

10 Claims, 5 Drawing Sheets

METHOD FOR REUSING AND DYNAMICALLY FILTERING CONTENT FOR STRUCTURED DOCUMENT CONSTRUCTION

CROSS-REFERENCE TO RELATED APPLICATION

The present application is a U.S. nonprovisional patent application of, and claims priority under 35 U.S.C. § 119(e) to, U.S. provisional patent application Ser. No. 61/866,329, filed Aug. 15, 2013, which provisional patent application is incorporated by reference herein.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
| --- | --- | --- |
| ASCIFY.txt | Aug. 15, 2013 15:12 | 37473 |
| prog1.txt | Aug. 15, 2013 15:11 | 22478848 |
| prog2.txt | Aug. 15, 2013 15:11 | 22478848 |
| prog3.txt | Aug. 15, 2013 15:11 | 22478848 |
| prog4.txt | Aug. 15, 2013 15:11 | 17998502 |
| readme.txt | Aug. 15, 2013 15:12 | 2713 |

One of these files, "readme.txt", contains instructions for extracting information from other of the files. These other files represent a compressed binary file that have been converted to ascii format. These files can be converted back to a compressed .zip archive utilizing an assembly conversion program source code for which is contained in "ascify.txt". The readme file includes instructions for compiling and running this conversion program, and instructions for converting the other text files to a compressed, binary file.

Some of these compressed, binary files include source code written in C Sharp that can be compiled utilizing Microsoft Visual Studio. The target environment for implementations utilizing such source code is 32-bit or 64-bit Windows XP, Vista, or 7.

BACKGROUND OF THE INVENTION

The present invention relates to electronic documents. More specifically, the present invention relates to the dynamically updating electronic documents based on context.

There are many different types of notes or clinical documents produced during an ambulatory clinical encounter. Examples could include: a new patient visit, charting the progress of a patient's chronic illness, or documenting a procedure. These documents may have different regulatory or business workflows that they must adhere to during their lifecycle, have different security requirements or may only be applicable to specific specialties. Further each document may capture different types of data such as a patient's chief complaint, the provider's review of systems or physical exam, the patient's history of present illness, or the provider's assessment and plan. These different note types are system specific. However, within that system, the note types could be applicable to the entire patient population.

Current systems require that the document structure be explicitly tied to the clinical content during administration. The problem with this is that the document structure is explicitly tied to the clinical content during administration. Therefore, document templates and forms cannot evolve independently of each other. For example, if an administrator wants to add a new form, he/she would have to visit every document template and update it with the new form.

Therefore, there exists a need for an improved method for sharing common workflows across document types within a system, as well as sharing content across systems. This, and other needs are addressed by one or more aspects of the present invention.

SUMMARY OF THE INVENTION

The present invention includes many aspects and features. Moreover, while many aspects and features relate to, and are described in, the context of tablet computing, the present invention is not limited to use only in this context, as will become apparent from the following summaries and detailed descriptions of aspects, features, and one or more embodiments of the present invention.

Accordingly, one aspect of the present invention relates to a method for dynamically constructing a pre-populated note template comprising receiving a context from a user and determining whether there are any note templates that match an initial criteria including the received context. A note template is then loaded based on the determination of matching note templates. If there are one or more sections in the loaded template, for each section in the loaded template, determine if there are any forms for the section that match the context. A pre-populated Note template is then loaded including any matching forms.

In a feature of this aspect, the context includes a user's context and a patient's context.

In another feature of this aspect, the user's context is a user's specialty and the patient's context is a patient's demographics.

In another feature of this aspect, the method further comprises receiving a selection by the user of a patient, receiving the user's specialty, and receiving the patient's demographics.

In another feature of this aspect, the method further comprises displaying a list of available note templates that match the initial criteria, and receiving an indication from the user of a selected one of the available note templates.

In another feature of this aspect, a default note template is loaded when it is determined that there are no matching note templates.

In another feature of this aspect, for each determined matching form, determine if the form requires patient chart data, retrieve patient chart data for the matching form, and pre-populate the respective section with the matching form, including the chart data.

In another feature of this aspect, for each determined matching form that does not require patient chart data, determine if the matching form requires discrete item filtering, filter the required discrete items, and pre-populate the respective section with the filtered form.

In another feature of this aspect, the pre-populated note template includes the pre-populated sections.

Another aspect of the present invention relates to a system comprising a computing device having a processor, the processor comprising a plurality of computer readable instructions for implementing a method for dynamically constructing and displaying a pre-populated note template. The method comprises receiving a context from a user and determining whether there are any note templates that match an initial criteria including the received context. A note template is then loaded based on the determination of matching note templates. If there are one or more sections in the loaded template, for each section in the loaded template, determine if there are any forms for the section that match the context. A pre-populated Note template is then loaded including any matching forms.

Another aspect of the present invention relates to a computing device having a processor, the processor comprising a plurality of computer readable instructions for implementing a method for receiving a dynamically constructed pre-populated note template. The method comprises selecting a new Note, inputting context information, selecting a Note template from a list of available Note templates, and receiving a pre-populated Note template for data entry.

In a feature of this aspect, the context information comprises a user context and a patient context.

In another feature of this aspect, the user context includes a user's specialty, and the patient context includes a patient's demographics.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Referring now to the drawings, one or more preferred embodiments of the present invention are next described. The following description of one or more preferred embodiments is merely exemplary in nature and is in no way intended to limit the invention, its implementations, or uses.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

As described above, different note types may be system specific. However, within that system, the notes types may be applicable to a provider's entire patient population. As such, the system agnostic content that is captured within general documents can be sub-divided and dynamically loaded based on the current context in which the documentation is taking place. Content in this context refers to the predefined text or discrete data capture form specific to the patient or documentation scenario. For example, a provider may want to document the progress of a patient's angina. The progress note type may then include a history of present illness sub section and the chest pain content form would be dynamically inserted, based on the patient demographics and provider specialty, into the document.

Separating this content from the document structure allows for the reuse of common workflows across document types within a system as well as sharing content across systems.

Accordingly, a computer implemented system and method are disclosed for dynamically constructing a clinical template and presenting the template to a user, e.g., a healthcare provider. The system includes a computing device having a processor that executes the method via an application (software) comprising a set of machine readable code stored on a machine readable medium and executable on the computing device.

In accordance with one aspect of the disclosed system, the process for dynamically generating the template begins with the context, i.e., user context and patient context. The user context includes, for example, the user's rights and permissions and his/her specialty that is defined within the base system. The patient context includes, for example, the patient's demographics (age and sex) as well as a patient identifier, in which patient data can be obtained, e.g., the patient's current health problem or medication list.

In order for the system to construct a document that a user can use, a document template must first exist. An example pseudo XML representation of a document template may look like the following:

```
<documenttemplate name="Progress Note"
    specialties="Internal Medicine, Oncology, Pediatrics"
    sex="male" agerange="2years-125years" signingau-
    thority="6" createtaskonfinalization="true">
<sections>
<section name="Chief Complaint" type="CC"/>
<section name="Medical History" type="MH"/>
<section name="History of Present Illness"
    type="HPI"/>
<section name="Review of Systems" type="ROS"/>
</sections>
</documenttemplate>
```

This example defines the structure of a document and the system or organization specific business rules associated with how to handle this type of clinical note. The document structure is defined via the sections listed and the business rules are represented by document attributes such as "signingauthority" and "createtaskonfinalization", for example. Further, the example template generated by the pseudo XML includes attributes that can be used for filtering so that users are only presented with templates that match their specialty or their patients' demographics. Accordingly, each organization or system may have different document structures, different workflow implementations or different requirements for document filtering. The separation of the section content from the document structure allows the content to be reused across systems or organizations without duplicating that content for each document type.

Once a document template is defined, system agnostic content forms can be created and dynamically inserted into a document template's section placeholders. For example, a form type could be a free text form, represented below in pseudo XML:

```
<form name="General Free Text" type="FT"
    specialties="ALL" sex="ALL" agerange="ALL">
<paragraphs>
<paragraph>
<text />
</paragraph>
</paragraphs>
</form>
```

Preferably, each form has a name, a type and the same specialty and demographic filters available to document templates. In the example above, the 'General Free Text' form is available for all specialties and all patients. Further it has a paragraphs collection with a single paragraph and an empty text placeholder.

At runtime when a document template is loaded and its sections are enumerated, the system determines which section types are mapped to which form types using a look up table. For example, if the 'Progress Note' document template, exemplified above, passed an initial filter criteria, the system then reviews each section defined in the document template and determines if there are any forms available for that section type that also pass the initial filter criteria. The form type/section type look up table is preferably the link that ties forms to sections, but also allows specific forms and sections to be decoupled from each other.

In addition to initial document template filtering and content form filtering, the disclosed system can dynamically load patient specific content or dynamically filter further within a form. Below is an example pseudo XML representation of a form that defines which clinical content should be automatically inserted into a section:

```
<form name="General Medical History" type="CL" specialties="ALL"
sex="ALL" agerange="ALL">
<paragraphs>
<paragraph name="Allergies">
<citedlistdetails>
<citedlistdetail tablename="dbo.allergies">
<columns>
<column name="name" displayorder="0"/>
<column name="onsetdate" displayorder="1"/>
<column name="description" displayorder="2"/>
</columns>
</citedlistdetail>
```

-continued

```
        </citedlistdetails>
    </paragraph>
    <paragraph name="Medications">
        <citedlistdetails>
            <citedlistdetail tablename="dbo.meds">
                <columns>
                    <column name="name" displayorder="0"/>
                    <column name="prescriptiondate" displayorder="1"/>
                    <column name="sig" displayorder="2"/>
                </columns>
``` defines two paragraphs, Allergies and Medications, and defines which table/view in the base system those data elements should come from. It further defines which columns should be included in the data set that is inserted for each item.

Another example form type may deal with discrete data and provides the user with a predefined set of questions. An example of this form type is represented in pseudo XML below:

```
<form name="General Review of Systems" type="QA" specialties="ALL" agerange="ALL">
    <paragraphs>
        <paragraph name="Constitutional">
            <text>Positive for {0}. Negative for {1}</text>
            <responsesinparagraph>
                <responseinparagraph responseID="0" paragraphposition="0"/>
                <responseinparagraph responseID="1" paragraphposition="1"/>
                <responseinparagraph responseID="2" paragraphposition="0"/>
                <responseinparagraph responseID="3" paragraphposition="1"/>
                <responseinparagraph responseID="4" paragraphposition="0"/>
                <responseinparagraph responseID="5" paragraphposition="1"/>
                <responseinparagraph responseID="6" paragraphposition="0"/>
                <responseinparagraph responseID="7" paragraphposition="1"/>
            </responsesinparagraph>
        </paragraph>
    </paragraphs>
    <observations>
        <observation name="Fever" type="boolean">
            <responses>
                <response id="0" name="Positive for fever infant response" value="true" text="infant fever" speciality="ALL" sex="ALL" agerange="0-24 months"/>
                <response id="1" name="Negative for fever infant response" value="False" text="infant fever" speciality="ALL" sex="ALL" agerange="0-24 months"/>
                <response id="2" name="Positive for fever All response" value="true" text="fever " speciality="ALL" sex="ALL" agerange="24 months - 125 years"/>
                <response id="3" name="Negative for fever All response" value="False" text="fever " speciality="ALL" sex="ALL" agerange="24 months - 125 years"/>
            </responses>
        </observation>
        <observation name="Chills" type="boolean">
            <responses>
                <response id="4" name="Positive for chills response" value="true" text="chills" speciality="ALL" sex="ALL" agerange="0 - 125 years"/>
                <response id="5" name="Negative for chills response" value="False" text="chills" speciality="ALL" sex="ALL" agerange="0 - 125 years"/>
            </responses>
        </observation>
        <observation name="Weight loss" type="boolean">
            <responses>
                <response id="6" name="Positive for weight loss response" value="true" text="weight loss" speciality="ALL" sex="ALL" agerange="0 - 125 years"/>
                <response id="7" name="Negative for weight loss response" value="False" text="weight loss" speciality="ALL" sex="ALL" agerange="0 - 125 years"/>
            </responses>
        </observation>
    </observations>
</form>
```

-continued

```
            </citedlistdetail>
        </citedlistdetails>
    </paragraph>
    </paragraphs>
</form>
```

In this example, the 'General Medical History' form is defined for all specialties and all patients. When a document template section is loaded that accepts form types of 'CL', this form will be pulled in after the cited list detail sections have been resolved against the current patient. This example The example 'General Review of Systems' form, as defined above, is applicable to all specialties and all patients. The form defines a single paragraph named 'Constitutional' and provides a pre-defined template text block. The example form also includes a set of observations (questions) and the available responses (answers) that may be applicable to this form. In this form, the responses can also be filtered by specialty and demographic match. These responses are tied to the paragraph text in question via the paragraph's responsesinparagraph collection.

After the document template and form have been matched based on the filter criteria, the system then filters out any responses that don't apply, effectively removing any questions that have zero responses. Accordingly, in this example the Fever observation has a set of Boolean responses for infants and non-infants, and if the patient is an infant and the user assesses that the patient has a fever, the system will display pre-defined text specific to infants.

Figure 1:
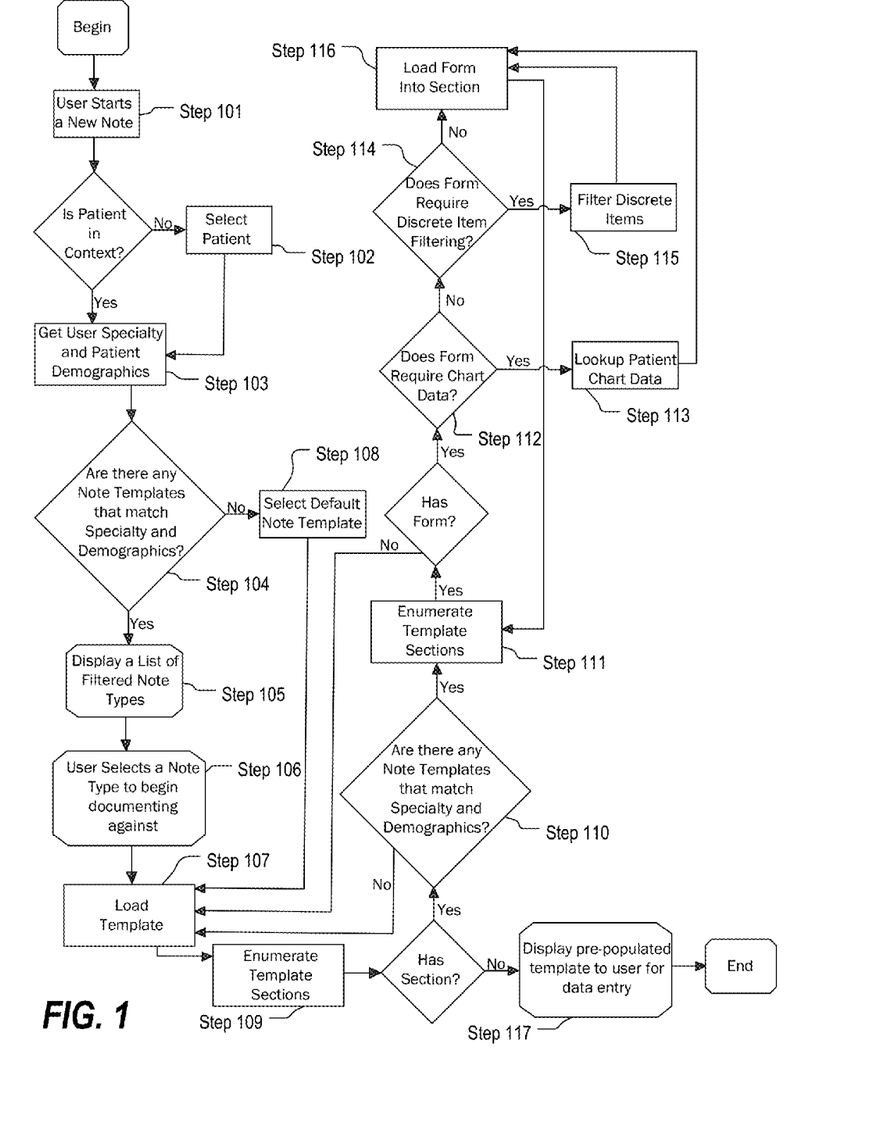
FIG. 1 illustrates an example flow diagram of the disclosed method for dynamically constructing a clinical template and presenting the template to a user.

An example flow diagram of the disclosed method is illustrated in FIG. 1. A user logs into the system through the graphical user interface (GUI) displayed on a computing device, for example, a desktop computer or mobile device, such as a laptop or tablet, and starts a new Note. Step 101. The patient that the user has encountered is selected, Step 102, and the user's specialty and patient demographics are retrieved. Step 103. If the patient was previously identified by the user, the system retrieves the user's specialty and patient demographics when the Note is started. Step 103.

A determination is then made as to whether there are any Note Templates that match the user's specialty and the patient's demographics. Step 104. If there are templates available, a list of filtered Note types is displayed to the user. Step 105. The user selects a Note template from the list, Step 106. The template is then loaded. Step 107.

Figure 2:
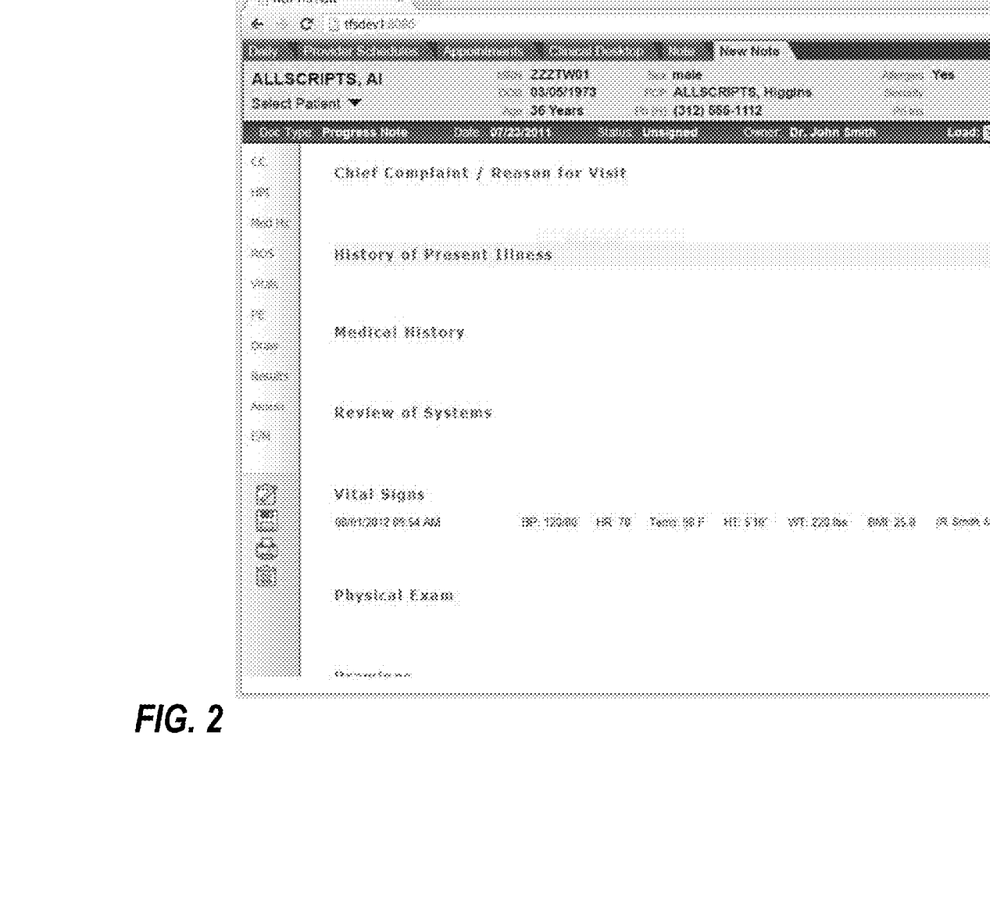
FIG. 2 illustrates an example screenshot of an empty progress note.

If there are no templates that match, a default Note is retrieved, Step 108, and displayed to the user. Step 107. An illustration of an example screen shot of a clinical Note template is shown in FIG. 2. As shown, the document structure of this template includes ten (10) sections: Chief Complaint, History of Present Illness, Medical History, Review of Systems, Vitals, Physical Exam, Draw, Results, Assess, and E/M. These sections did not contain any content except the Viatls section which was dynamically inserted based on the Patient context.

The system then determines whether there are any sections in the selected template. Step 109. If there are no sections in the template, a pre-populated template is displayed to the user. Step 117.

If there are sections within the template, a determination is made as to whether there are any forms available for each of the determined sections that match the initial filter criteria, e.g., specialty and patient demographics, for each determined section. Step 110. If there are one or more forms available for a section, each form is enumerated, Step 111, and a determination is made as to whether the form requires patient chart data, Step 112. If chart data is required, the patient chart data is retrieved, Step 113, and the form loaded into the section. Step 116.

If chart data is not required, a determination is made as to whether the form requires discrete item filtering, Step 114. If discrete item filtering is required, the appropriate discrete items are filtered, as disclosed above, Step 115, and the form loaded into the section. Step 116.

If the form does not require chart data or discrete item filtering, the form is loaded into the section. Step 116.

Once there are no longer any sections in the template to enumerate, the pre-populated template is displayed to the user for data entry. Step 117.

Figure 3:
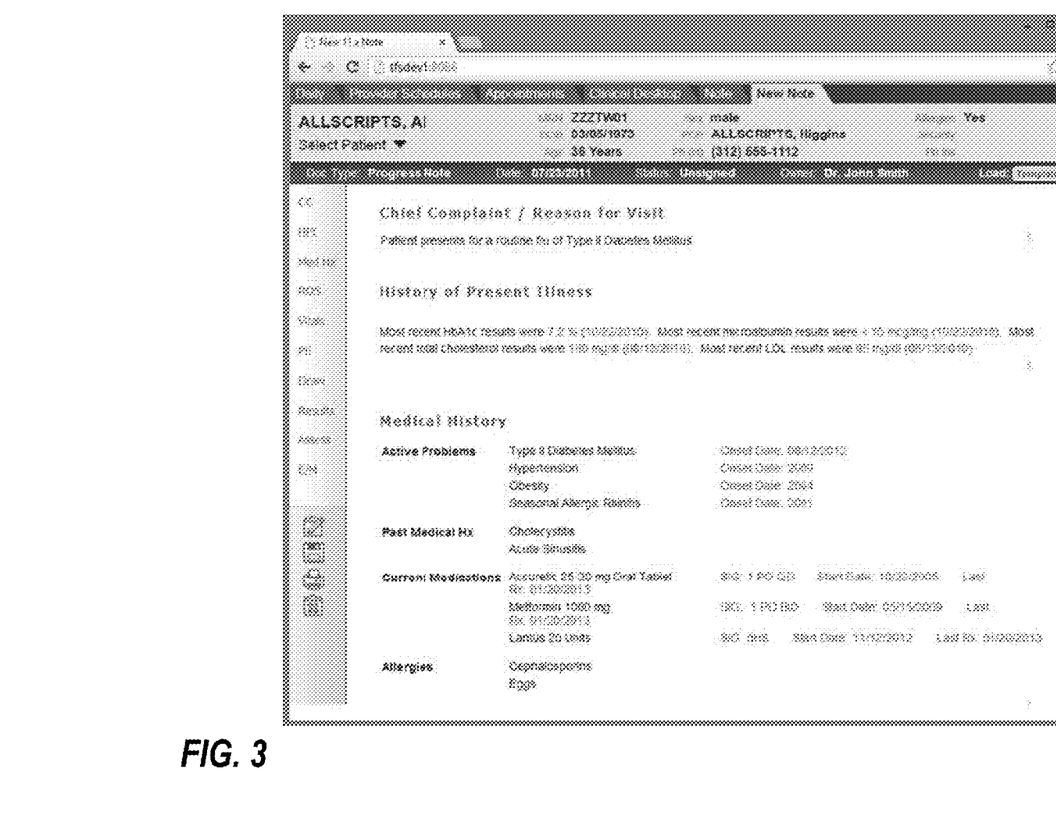
FIG. 3 illustrates the example progress note of FIG. 2 pre-populated based on a patient's history.

Example screenshots that illustrate the disclosed system and method. As described above, FIG. 2 is an illustration of an example screen shot of a clinical Note template. FIG. 3 is an illustration of the clinical Note template dynamically pre-populated based on a patient's history of Type II Diabetes Mellitus. As illustrated, the chief complaint and HPI sections have had text automatically inserted. Also, the Medical History section has been populated with relevant content pertinent to Diabetes.

Figure 4:
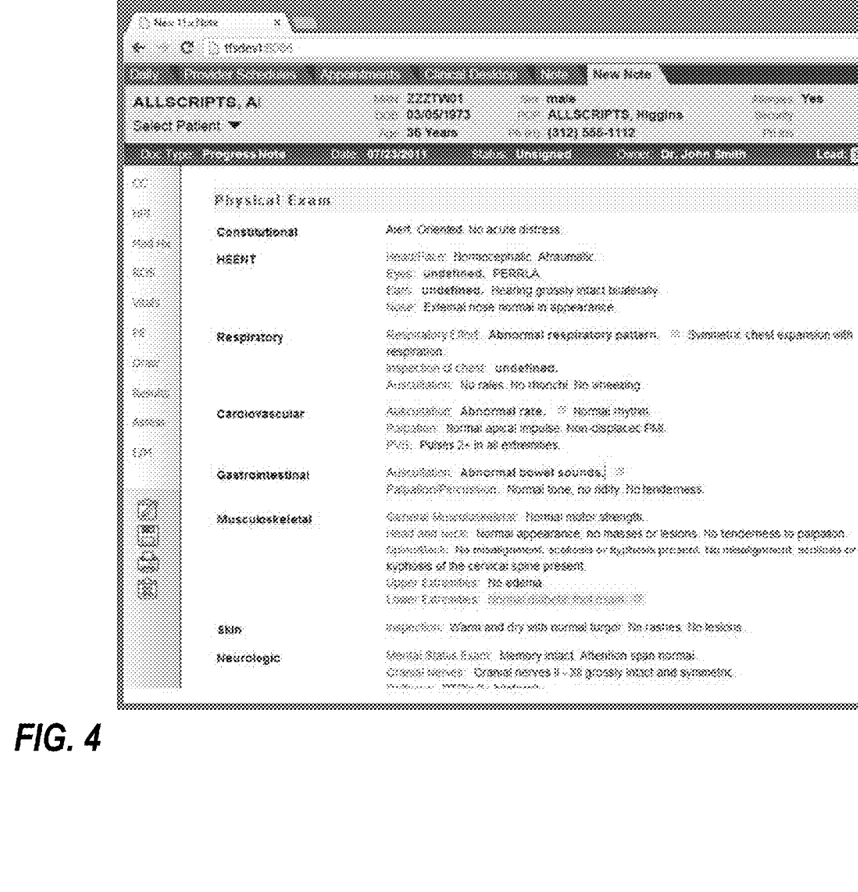
FIG. 4 illustrates the note of FIG. 3 with the physical exam section dynamically inserted.

FIG. 4 illustrates the Note shown in FIG. 3 including the insertion of the physical exam section including defaulted negative observation findings specific to Diabetes.

Figure 5:
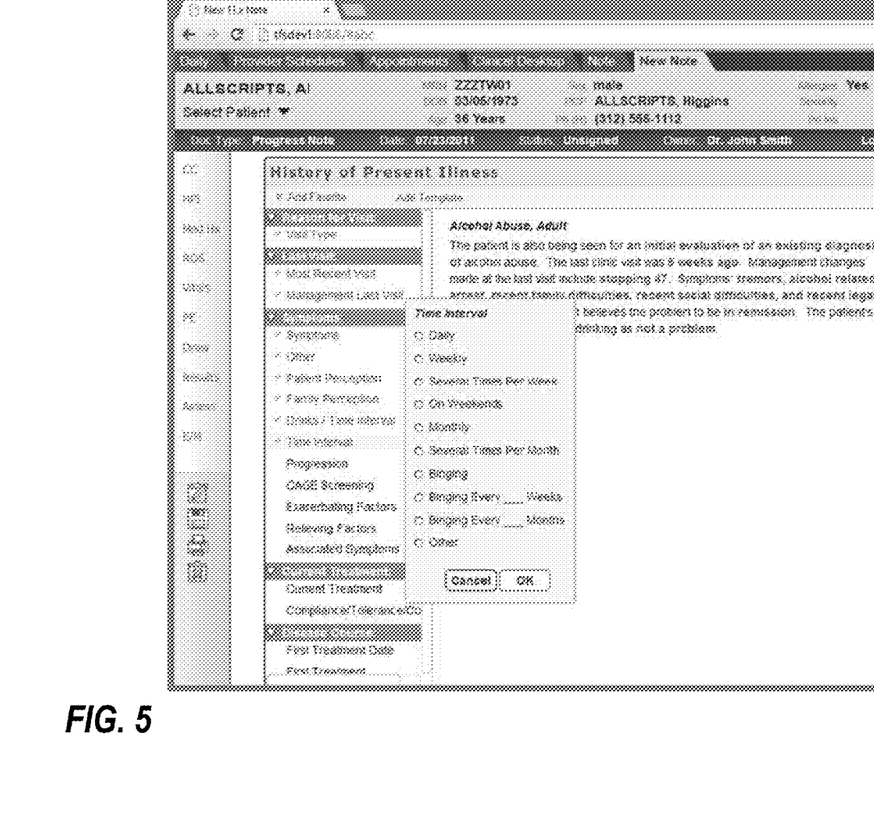
FIG. 5 illustrates an example screenshot of the manual import of clinical content that is dynamically chosen based on the context.

FIG. 5 is an example illustration of the manual inclusion of an HPI clinical content form for Alcohol Abuse. Based on the user's context and patient demographics, the system dynamically chose an Adult Alcohol Abuse form since the patient, A1 Allscripts, is 36 years old. The observations presented in this example form could be further filtered based on the patient's sex or provider's specialty. This type of inclusion illustrates how the clinical content can be reused independent of the document template which included the document structure as well as any system specific workflow and security that was defined by the system administrator.

The disclosed system and method has many advantages. One advantage is that content can be reused by decoupling system workflows and business rules associated with clinical documentation. Content forms may be shared across systems even when those systems have specialized and custom workflows.

Another advantage is that the dynamic filtering reduces administration burdens of existing systems by allowing global configurations to be automatically adapted to the situation at hand. Administrators no longer have to create and maintain multiple document type configurations when those types differ by content.

The disclosed system also allows the responses (answers) for observations (questions) to be filtered. The user of the system may then focus their attention on the appropriate responses and lessens the likelihood of accidentally selecting invalid response. These lists of observations and answers may then be re-used across forms, and the responses re-used across observations.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for dynamically constructing a pre-populated note template comprising the steps of:
   (I) maintaining
      (a) a plurality of document templates each including
         (i) one or more defined document attributes for use in filtering, and
         (ii) one or more defined document sections each associated with a section type;
      (b) a plurality of content forms each including
         (i) one or more defined form attributes for use in filtering, and
         (ii) a form type; and
      (c) a lookup table mapping section types to form types;
   (II) first,
      (a) determining, based on a login of a healthcare practitioner user, first user context information;

(b) determining, based on selection of a first patient, first patient context information for the first patient;
(c) determining, by comparing the determined first user context information and the determined first patient context information to the defined document attributes for each maintained document template, a first filtered list of one or more matching document templates;
(d) displaying the first filtered list of one or more matching document templates;
(e) receiving user input corresponding to first selection of a document template from the first filtered list of one or more matching document templates;
(f) for each respective defined section of the first selected document template, determining a respective matching content form for that respective defined section of the first selected document template by
  (i) determining, based on the maintained lookup table, respective one or more form types mapped to the section type of that respective defined section, and
  (ii) determining, by comparing the determined first user context information and the determined first patient context information to the defined form attributes for each content form having a form type corresponding to one of the determined respective one or more form types, the respective matching content form for that respective defined section of the first selected document template,
  (iii) wherein the determined matching content form for one of the defined sections of the first selected document template is a first maintained content form; and
(g) generating a first note comprising a first plurality of sections,
  (i) wherein the first note is generated utilizing the first selected document template and each of the determined matching content forms for the defined sections of the first selected document template, including the first maintained content form,
  (ii) wherein each section of the first plurality of sections
    (A) corresponds to a respective one of the defined sections of the first selected document template, and
    (B) is generated based on the corresponding determined matching content form for that respective one of the defined sections of the first selected document template,
  (iii) wherein a first section of the first note is generated based on the first maintained content form, and
  (iv) wherein the first note is pre-populated with patient information for the first patient; and
(III) thereafter,
  (a) determining, based on a login of a healthcare practitioner user, second user context information;
  (b) determining, based on selection of a second patient, second patient context information for the second patient;
  (c) determining, by comparing the determined second user context information and the determined second patient context information to the defined document attributes for each maintained document template, a second filtered list of one or more matching document templates;
  (d) displaying the second filtered list of one or more matching document templates;
  (e) receiving user input corresponding to second selection of a document template from the second filtered list of one or more matching document templates;
  (f) for each respective defined section of the second selected document template, determining a respective matching content form for that respective defined section of the second selected document template by
    (i) determining, based on the maintained lookup table, respective one or more form types mapped to the section type of that respective defined section, and
    (ii) determining, by comparing the determined second user context information and the determined second patient context information to the defined form attributes for each content form having a form type corresponding to one of the determined respective one or more form types, the respective matching content form for that respective defined section of the second selected document template,
    (iii) wherein the determined matching content form for one of the defined sections of the second selected document template is the first maintained content form; and
  (g) generating a second note comprising a second plurality of sections,
    (i) wherein the second note is generated utilizing the second selected document template and each of the determined matching content forms for the defined sections of the second selected document template, including the first maintained content form,
    (ii) wherein each section of the second plurality of sections
      (a) corresponds to a respective one of the defined sections of the second selected document template, and
      (B) is generated based on the corresponding determined matching content form for that respective one of the defined sections of the second selected document template,
    (iii) wherein a second section of the second note is generated based on the first maintained content form, and
    (iv) wherein the second note is pre-populated with patient information for the second patient;
(IV) wherein,
  (a) the first selected document template is a different maintained document template than the second selected document template, and
  (b) the first maintained content form is utilized to generate both the first section of the first note and the second section of the second note.

2. The method of claim 1, wherein the first patient context comprises patient demographic information.

3. The method of claim 1, wherein the first user context comprises a user's specialty.

4. The method of claim 1, further comprising retrieving patient chart data for pre-populating a form.

5. The method of claim 1, further comprising a discrete filtering methodology.

6. A system comprising a computing device having a processor, the processor comprising a plurality of computer readable instructions for implementing a method for dynamically constructing and displaying a pre-populated note template, the method comprising:
(I) maintaining
  (a) a plurality of document templates each including
    (i) one or more defined document attributes for use in filtering, and
    (ii) one or more defined document sections each associated with a section type;
  (b) a plurality of content forms each including
    (i) one or more defined form attributes for use in filtering, and
    (ii) a form type; and
  (c) a lookup table mapping section types to form types;
(II) first,
  (a) determining, based on a login of a healthcare practitioner user, first user context information;
  (b) determining, based on selection of a first patient, first patient context information for the first patient;
  (c) determining, by comparing the determined first user context information and the determined first patient context information to the defined document attributes for each maintained document template, a first filtered list of one or more matching document templates;
  (d) displaying the first filtered list of one or more matching document templates;
  (e) receiving user input corresponding to first selection of a document template from the first filtered list of one or more matching document templates;
  (f) for each respective defined section of the first selected document template, determining a respective matching content form for that respective defined section of the first selected document template by
    (i) determining, based on the maintained lookup table, respective one or more form types mapped to the section type of that respective defined section, and
    (ii) determining, by comparing the determined first user context information and the determined first patient context information to the defined form attributes for each content form having a form type corresponding to one of the determined respective one or more form types, the respective matching content form for that respective defined section of the first selected document template,
    (iii) wherein the determined matching content form for one of the defined sections of the first selected document template is a first maintained content form; and
  (g) generating a first note comprising a first plurality of sections,
    (i) wherein the first note is generated utilizing the first selected document template and each of the determined matching content forms for the defined sections of the first selected document template, including the first maintained content form,
    (ii) wherein each section of the first plurality of sections
      (a) corresponds to a respective one of the defined sections of the first selected document template, and
      (b) is generated based on the corresponding determined matching content form for that respective one of the defined sections of the first selected document template,
    (iii) wherein a first section of the first note is generated based on the first maintained content form, and
    (iv) wherein the first note is pre-populated with patient information for the first patient; and
(III) thereafter,
  (a) determining, based on a login of a healthcare practitioner user, second user context information;
  (b) determining, based on selection of a second patient, second patient context information for the second patient;
  (c) determining, by comparing the determined second user context information and the determined second patient context information to the defined document attributes for each maintained document template, a second filtered list of one or more matching document templates;
  (d) displaying the second filtered list of one or more matching document templates;
  (e) receiving user input corresponding to second selection of a document template from the second filtered list of one or more matching document templates;
  (f) for each respective defined section of the second selected document template, determining a respective matching content form for that respective defined section of the second selected document template by
    (i) determining, based on the maintained lookup table, respective one or more form types mapped to the section type of that respective defined section, and
    (ii) determining, by comparing the determined second user context information and the determined second patient context information to the defined form attributes for each content form having a form type corresponding to one of the determined respective one or more form types, the respective matching content form for that respective defined section of the second selected document template,
    (iii) wherein the determined matching content form for one of the defined sections of the second selected document template is the first maintained content form; and
  (g) generating a second note comprising a second plurality of sections,
    (i) wherein the second note is generated utilizing the second selected document template and each of the determined matching content forms for the defined sections of the second selected document template, including the first maintained content form,
    (ii) wherein each section of the second plurality of sections
      (a) corresponds to a respective one of the defined sections of the second selected document template, and
      (b) is generated based on the corresponding determined matching content form for that respective one of the defined sections of the second selected document template,
    (iii) wherein a second section of the second note is generated based on the first maintained content form, and (iv) wherein the second note is pre-populated with patient information for the second patient;

(IV) wherein,
  (a) the first selected document template is a different maintained document template than the second selected document template,
  (b) the first maintained content form is utilized to generate both the first section of the first note and the second section of the second note.

7. The system of claim 6, wherein the first patient context comprises patient demographic information.

8. The system of claim 6, wherein the first user context comprises a user's specialty.

9. The system of claim 6, further comprising retrieving patient chart data for pre-populating a form.

10. The system of claim 6, further comprising a discrete filtering methodology.

* * * * *